(12) United States Patent
Estevez et al.

(10) Patent No.: US 11,534,230 B2
(45) Date of Patent: Dec. 27, 2022

(54) MEDICAL DEVICES AND RELATED METHODS

(71) Applicant: Boston Scientific Scimed, Inc., Maple Grove, MN (US)

(72) Inventors: Ramon Estevez, Lowell, MA (US); Mingxiang Xu, Wayland, MA (US); Paul Smith, Smithfield, RI (US); Irina Pyataeva, Moscow (RU); Kevin McElwee, Franklin, MA (US); Allyn Jensrud, Brookline, MA (US); Jose Garcia-Cordero, Ocala, FL (US); Samuel Raybin, Marlborough, MA (US); Jennifer Heywood, Hudson, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 444 days.

(21) Appl. No.: 16/364,835

(22) Filed: Mar. 26, 2019

(65) Prior Publication Data

US 2019/0298435 A1    Oct. 3, 2019

Related U.S. Application Data

(60) Provisional application No. 62/648,444, filed on Mar. 27, 2018.

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *A61B 18/148* (2013.01);
(Continued)

(58) Field of Classification Search
CPC ... A61B 18/14; A61B 18/148; A61B 18/1206; A61B 2018/1475; A61B 2018/00589;
(Continued)

(56) References Cited

U.S. PATENT DOCUMENTS 5,688,267 A * 11/1997 Panescu ................. A61N 1/403
606/41
5,807,395 A    9/1998 Mulier et al.
(Continued)

FOREIGN PATENT DOCUMENTS

EP    1007111 A1    6/2000
EP    2001384 A1    12/2008

OTHER PUBLICATIONS

Huang et al., "Comparison of O-Type HybridKnife to Conventional Knife in Endoscopic Submucosal Dissection for Gastric Mucosal Lesions", Apr. 1, 2016, p. 1-6, vol. 95, No. 13, Medicine (Baltimore) (6 pages).
(Continued)

*Primary Examiner* — Linda C Dvorak
*Assistant Examiner* — Lindsay Regan Lancaster
(74) *Attorney, Agent, or Firm* — Bookoff McAndrews, PLLC

(57) ABSTRACT

A medical device includes a shaft including a central lumen configured to direct a flow of fluid through the shaft, and an electrode positioned at a distal portion of the shaft. The electrode includes an electrode lumen in fluid communication with the central lumen, and the electrode lumen is configured to receive the flow of fluid from the central lumen. The electrode also includes one or more channels angled relative to the electrode lumen, and the one or more channels are in fluid communication with the electrode lumen to receive the flow of fluid from the electrode lumen. The one or more channels are configured to divert the flow
(Continued)

of fluid from the electrode lumen toward one or more outlets laterally offset from the electrode lumen.

20 Claims, 8 Drawing Sheets

(51) Int. Cl.
*A61B 17/34* (2006.01)
*A61B 18/00* (2006.01)
*A61B 18/16* (2006.01)
*A61B 17/32* (2006.01)

(52) U.S. Cl.
CPC ........... *A61B 17/3478* (2013.01); *A61B 18/16* (2013.01); *A61B 2017/320044* (2013.01); *A61B 2018/00011* (2013.01); *A61B 2018/00065* (2013.01); *A61B 2018/00196* (2013.01); *A61B 2018/00577* (2013.01); *A61B 2018/00589* (2013.01); *A61B 2018/00595* (2013.01); *A61B 2018/00601* (2013.01); *A61B 2018/00607* (2013.01); *A61B 2018/00619* (2013.01); *A61B 2018/00738* (2013.01); *A61B 2018/1425* (2013.01); *A61B 2018/1475* (2013.01); *A61B 2218/002* (2013.01)

(58) Field of Classification Search
CPC ........... A61B 2018/00065; A61B 2018/00577; A61B 2018/00607; A61B 2218/002; A61B 2018/00196; A61B 18/16; A61B 2017/320044; A61B 17/3478; A61B 2018/00595; A61B 2018/1425; A61B 2018/00619; A61B 2018/00738; A61B 2018/00011; A61B 2018/00601
See application file for complete search history.

(56) References Cited

U.S. PATENT DOCUMENTS

| | | | | |
|---|---|---|---|---|
| 2004/0210284 | A1* | 10/2004 | Okada | A61B 18/1402 607/96 |
| 2008/0071267 | A1* | 3/2008 | Wang | A61B 18/1492 606/41 |
| 2008/0132888 | A1* | 6/2008 | Iida | B05B 17/0607 606/41 |
| 2008/0161795 | A1* | 7/2008 | Wang | A61B 18/1492 606/41 |
| 2010/0168728 | A1* | 7/2010 | Wang | A61B 18/18 606/33 |
| 2011/0009857 | A1* | 1/2011 | Subramaniam | A61B 18/1492 606/41 |
| 2012/0035607 | A1* | 2/2012 | Karwei | A61B 18/1482 606/46 |
| 2016/0220301 | A1* | 8/2016 | Yamamoto | A61B 18/12 |
| 2018/0271594 | A1* | 9/2018 | Tyson | A61B 18/14 |
| 2018/0333191 | A1* | 11/2018 | Greep | A61B 18/00 |
| 2020/0390494 | A1* | 12/2020 | Jeon | A61B 18/1492 |
| 2021/0113260 | A1* | 4/2021 | Tang | A61B 18/1492 |

OTHER PUBLICATIONS

International Search Report and Written Opinion issued in International Application No. PCT/US2019/024041, dated Jul. 2, 2019 (12 pages).

* cited by examiner

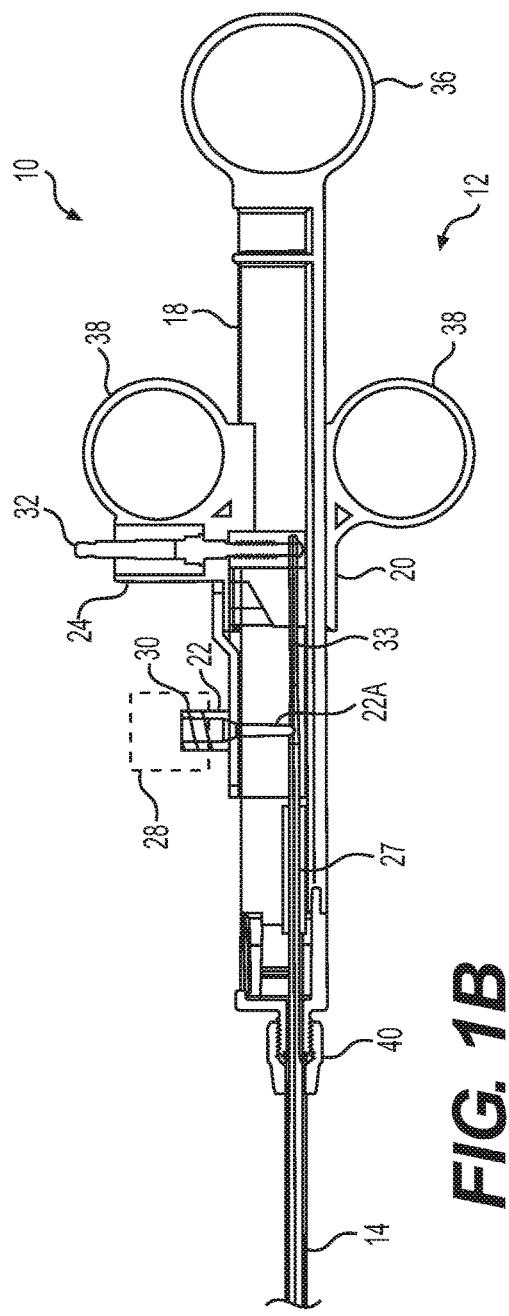
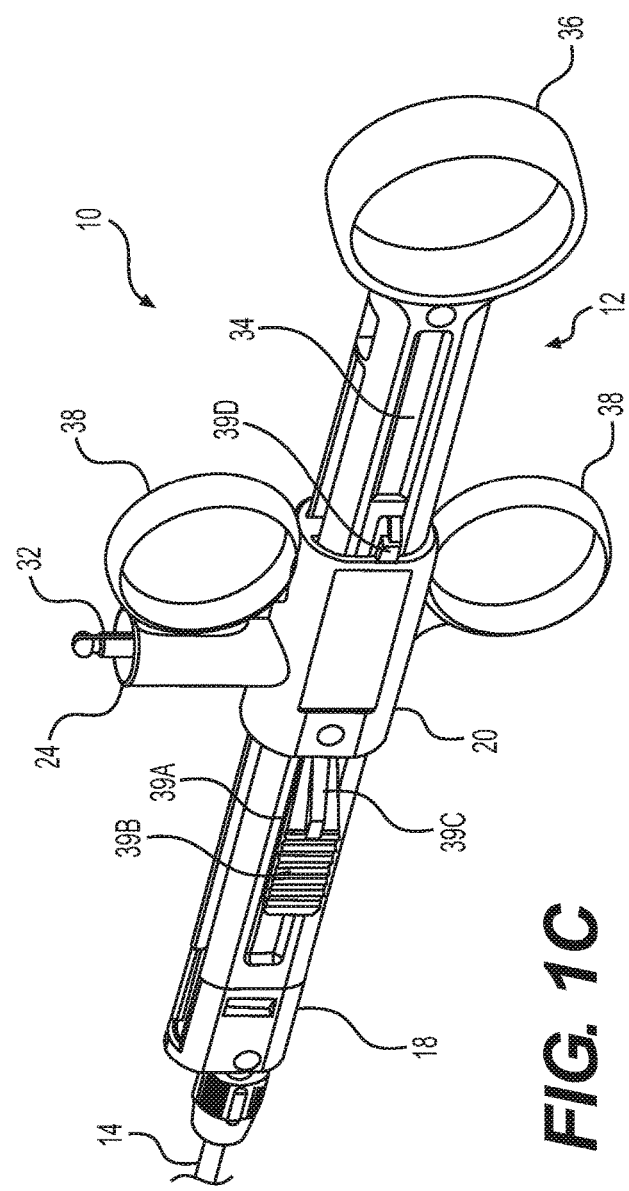
FIG. 1B
FIG. 1C

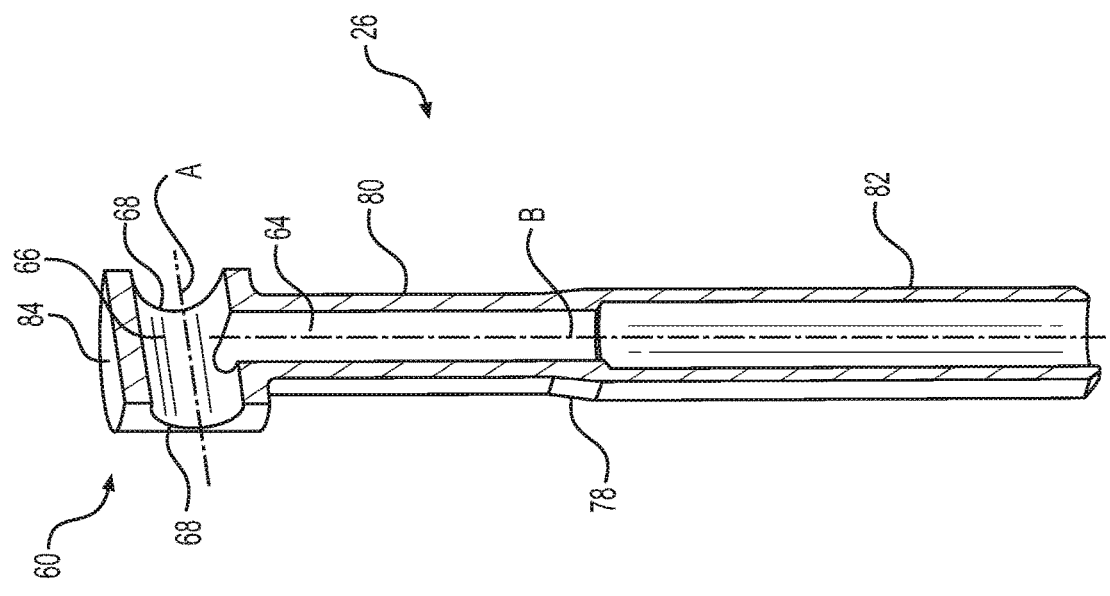
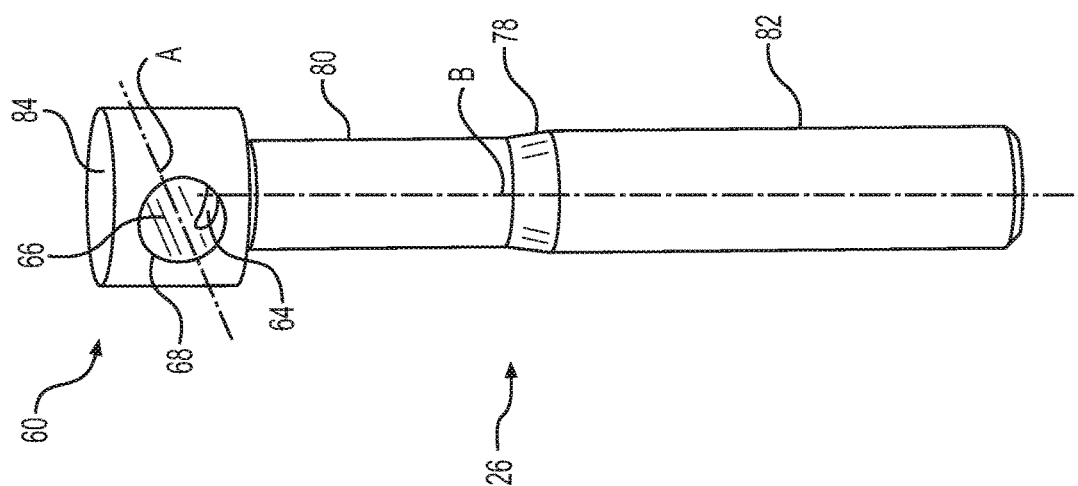
FIG. 3B
FIG. 3A

MEDICAL DEVICES AND RELATED METHODS

CROSS-REFERENCE TO RELATED APPLICATIONS

This patent application claims the benefit under 35 U.S.C. § 119 to U.S. Provisional Patent Application No. 62/648,444, filed on Mar. 27, 2018, the entirety of which is incorporated herein by reference.

TECHNICAL FIELD

Aspects of the present disclosure generally relate to medical devices and procedures. In particular, aspects of the present disclosure relate to medical devices and procedures for treating tissue by delivering electrical energy into tissue, and injecting fluid into and/or under tissue.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve delivering energy to tissue of an organ or a gland to treat tumors, infections, and the like. Examples of such procedures include Endoscopic Mucosal Resection (EMR), Endoscopic Sub-mucosal Resection (ESR), Endoscopic Sub-mucosal Dissection (ESD), polypectomy, mucosectomy, etc. In particular, such procedures may be carried out by inserting an insertion device into a patient's body through a surgical incision, or via a natural anatomical orifice (e.g., mouth, vagina, or rectum), and performing the procedure or operation at a target site with an auxiliary device inserted through the insertion device.

At times, during a medical procedure, a user may use an injection needle inserted through an insertion device to form (or re-form) a bleb in or under tissue to be removed. In order to deliver energy to the tissue, the user may be required to remove the injection needle from the insertion device and deliver an energy delivery device through the insertion device to the tissue being targeted. Additionally, during the procedure, the user may alternate using the injection needle and the energy delivery device. The exchange of devices may increase the duration and risks of the medical procedure.

The devices and methods of the current disclosure may rectify some of the deficiencies described above or address other aspects of the prior art.

SUMMARY

Examples of the present disclosure relate to, among other things, medical devices for treating tissue by delivering electrical energy to the tissue, and delivering fluid into and/or under the tissue, and related methods of use thereof. Each of the examples disclosed herein may include one or more of the features described in connection with any of the other disclosed examples.

In one example, a medical device may include a shaft including a central lumen configured to direct a flow of fluid through the shaft, and an electrode positioned at a distal portion of the shaft. The electrode may include an electrode lumen in fluid communication with the central lumen, and the electrode lumen may be configured to receive the flow of fluid from the central lumen. The electrode also may include one or more channels angled relative to the electrode lumen, and the one or more channels may be in fluid communication with the electrode lumen to receive the flow of fluid from the electrode lumen. The one or more channels may be configured to divert the flow of fluid from the electrode lumen toward one or more outlets laterally offset from the electrode lumen.

The medical device may further include one or more of the following features. The medical device may further include a handle with a main part and a movable part, and at least one of the main part and the movable part may include a slot. Sliding of the movable part in a first direction relative to the main part may extend the electrode, and sliding of the movable part in a second direction relative to the main part may retract the electrode. At least one of the main part and the movable part may include a fluid port to couple a fluid source to the handle, and at least one of the main part and the movable part may include a hub to couple an energy source to the handle. The medical device may further include a drive element. The drive element may extend from the handle to the electrode to electrically connect the energy source to the electrode, and to move the electrode distally or proximally based on relative movement between the main part and the movable part.

The medical device may further include a one way valve coupling the fluid source to the port and preventing fluid from flowing proximally out of the port. The shaft may include an electrically insulating sheath, and the sheath may be coupled to an electrically insulating distal end cap including a passage for slidably receiving the electrode. The electrode may include a distal tip having a closed distalmost end face, and the distal tip may include at least two outlets for emitting the fluid. The at least two outlets may be positioned proximal to the distalmost end face. One or more central longitudinal axes of the one or more channels may extend transverse to a central longitudinal axis of the electrode lumen. The one or more channels may extend in a V-shape to connect the electrode lumen to the two outlets. The distal tip may include four outlets, and the four outlets may be connected by two channels, the two channels extending in a direction transverse to the electrode lumen.

The electrode may include a distal tip. The one or more channels may include a plurality of indentations that connect a radial exterior of the distal tip to the electrode lumen. The electrode may further include an electrode cap that extends over a distal end of the electrode lumen such that fluid delivered through the electrode lumen flows through the indentations at an angle relative to a central longitudinal axis of the electrode lumen. The distal tip may include a cylindrical end portion that extends over a distal end of the electrode lumen. The one or more channels and one or more outlets may be formed by a plurality of side slits positioned proximal to the cylindrical end portion and connecting to the electrode lumen such that fluid delivered through the electrode lumen flows through the side slits at an angle relative to the central longitudinal axis of the electrode lumen.

The medical device may further include an insulating end cap surrounding at least a portion of the electrode. The end cap may include a narrowed stop surface radially surrounding a portion of the electrode. The electrode may include a widened portion proximal to a distal tip of the electrode, and the stop surface of the end cap and the widened portion of the electrode may limit the distal extension of the electrode.

In another example, a medical device may include a shaft including a central lumen configured to direct a flow of fluid through the shaft and an electrode positioned at a distal portion of the shaft and including an electrode lumen in fluid communication with the central lumen. The electrode lumen may be configured to receive the flow of fluid from the central lumen, and the electrode may include a central longitudinal axis. The electrode may include a distal tip with a plurality of channels fluidly connected to the electrode lumen. Each of the plurality of channels may include a central longitudinal axis, and at least one of the central longitudinal axes of the plurality of channels may be angled relative to the central longitudinal axis of the electrode lumen.

The medical device may further include one or more of the following features. A combined cross-sectional area of the plurality of channels may be greater than a cross-sectional area of the electrode lumen. The plurality of channels may include two channels, with the central longitudinal axes of the two channels extending in a V-shape and being angled relative to the central longitudinal axis of the electrode lumen by an acute angle. The distal tip may include a closed distalmost end face.

In a further example, a method of treating tissue may include inserting a medical device into a body lumen, and the medical device may include an electrode at a distal end. The electrode may include at least two fluid outlets positioned proximal to a distal face of the electrode, and at least one fluid outlet may include a central axis that is transverse to a central longitudinal axis of the electrode. The method may also include delivering fluid to a tissue portion within the body lumen, and the fluid may be delivered through the at least two outlets into the tissue portion and may be configured to at least partially move the tissue portion away from an underlying tissue layer. The method may further include energizing the electrode and applying the energized electrode to the tissue portion to deliver electrical energy to the tissue portion.

The method may further include one or more of the following features. The method may further include delivering fluid to the tissue portion another time after applying the energized electrode to the tissue portion. The method may further include contemporaneously delivering fluid and applying electrical energy to the electrode.

In one aspect, a method of treating tissue may include transferring fluid into tissue, where the fluid may be transferred into the tissue peripherally about an electrode, and where the transfer of the fluid moves at least one of an overlying layer of the tissue and an underlying layer of the tissue away from the other of the overlying layer and the underlying layer. The method may also include resecting the overlying layer.

The method may further include one or more of the following features. The transferring of the fluid into the tissue may include piercing the overlying layer with the electrode, and emitting the fluid from a plurality of side openings of the electrode. The resecting of the overlying layer may include energizing the electrode, and resecting the overlying layer with the energized electrode.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 1A-1C illustrate an exemplary medical device, according to aspects of this disclosure.

FIGS. 3A and 3B illustrate a perspective view and a cross-sectional view, respectively, of a portion of the medical device of FIG. 1, according to aspects of the present disclosure.

DETAILED DESCRIPTION

Examples of the present disclosure include devices and methods for: facilitating and improving the efficacy, efficiency, and safety of treating tissue when, for example, applying electrical energy to tissue; and delivering fluid into and/or under tissue during a medical procedure. For example, aspects of the present disclosure may provide a user (e.g., physician, medical technician, or other medical service provider) with the ability to apply electrical energy or heat to tissue using a medical device having an electrode, and to deliver fluid into and/or under tissue with the same medical device. Additionally, aspects of the present disclosure may provide the user with the ability to deliver fluid through one or more outlets, with the fluid being diverted on its way to the outlets (e.g., delivered at an angle relative to a central longitudinal axis of the electrode). Various aspects of the present disclosure may include the one or more outlets being positioned proximal to a distal tip or distal end face of the electrode. Some aspects of the present disclosure may be used in performing an endoscopic, laparoscopic, arthroscopic, or other type of procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to a medical professional using the medical device. In contrast, "distal" refers to a position relatively further away from the medical professional using the medical device, or closer to the interior of the body. As used herein, the terms "comprises," "comprising," "having," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Figure 1A:
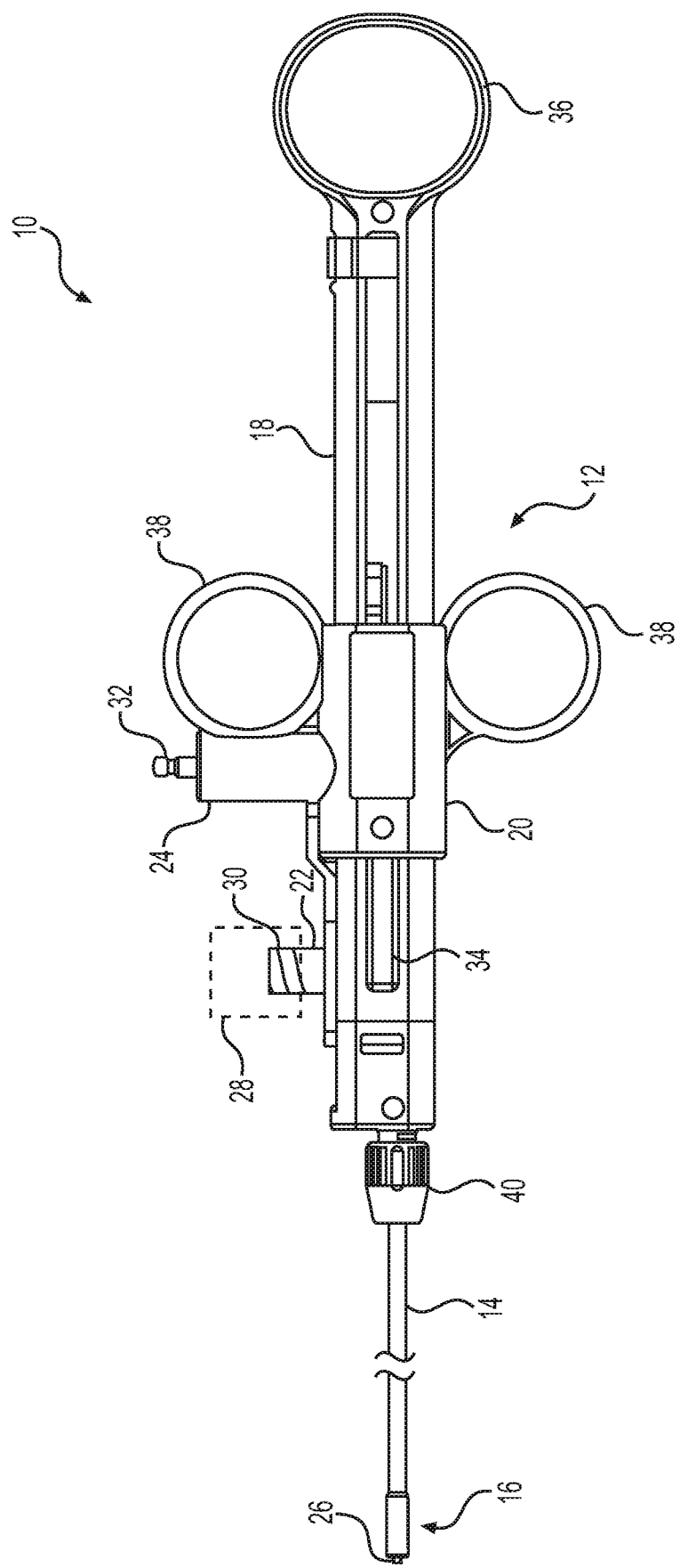

FIGS. 1A-1C depict a medical device 10 that includes a handle 12, a shaft 14, and a distal end 16. Handle 12 may include a main body 18 and a movable body 20. Handle 12 also may include a port 22 configured to receive fluid, and a hub 24 configured to receive electrical energy similar to an electrical plug or socket. Distal end 16 includes an electrode 26. Electrode 26 is electrically connected to hub 24, and includes one or more lumens (FIG. 2C) fluidly connected to port 22. Medical device 10 may be inserted into a body lumen of a subject, either through an insertion device (not shown) or alone, such that at least a portion of shaft 14 may be within the subject, while handle 12 may remain outside of the subject. From outside of the subject, a user can manipulate handle 12. Movement of movable body 20 relative to main body 18 in a first direction may extend electrode 26 relative to shaft 14 (e.g., move electrode 26 distally relative to a distal end of shaft 14), while movement of movable body 20 relative to main body 18 in a second direction may retract electrode 26 relative to shaft 14 (e.g., move electrode 26 proximally relative to a distal end of shaft 14).

Handle 12 may be coupled to a fluid source via port 22. Port 22 may be fluidly coupled to electrode 26 via an internal lumen 27 and through shaft 14. For example, as shown in FIG. 1B, internal lumen 27 may extend longitudinally through main body 18 of handle 12, and port 22 may include a port lumen 22A that extends through port 22 to fluidly connect port 22 to internal lumen 27. The fluid source may include an irrigation bag, vial, or other container or reservoir of a saline solution or other fluid. The fluid source may pressurize the fluid via a pump, an injection needle, a gravity drip, or other pressure source. The fluid source may be user controlled via a trigger, foot pedal, adjustable dial, or other control device, and/or may deliver an automatic or constant irrigation supply. In one aspect, a continuous irrigation supply may help to prevent clogs or blockages in the flowpath traveled by the fluid. Port 22 may be positioned on a distal portion of main body 18. Alternatively, port 22 may be positioned on movable body 20. Moreover, port 22 may include a one-way valve 28, a luer, a seal, threading 30, or any appropriate element to maintain a secure connection between handle 12 and the fluid source, minimize or prevent back-flow (e.g., fluid flowing proximally out of port 22), and/or minimize or prevent leakage. In one example, one-way valve 28 may include an outer housing containing an inner elastomeric and/or gelatinous sealing member (not shown).

Handle 12 may be coupled to an energy source through hub 24. Hub 24 may be electrically coupled to electrode 26 via a conductive element in shaft 14. The energy source may be an electrocautery source, an RF generator, a heating source, a current generator, etc. In one aspect, medical device 10 may be used for a monopolar electrosurgery procedure, and may include a return electrode positioned remotely from electrode 26. As discussed with the fluid source, the energy source may include any control element to allow a user to control the delivery of the energy. Hub 24 may be positioned on movable body 20 and may include one or more pins or prongs 32 to couple to the energy source. Alternatively, hub 24 may be positioned on main body 18. In one aspect shown in FIG. 1B, prong 32 may extend through hub 24 transverse to a longitudinal axis of handle 12, and may be electrically and physically connected to a conductive element 33, such as a wire, a cable, and/or a braided sheath. Conductive element 33 may be electrically conductive or include an electrically conductive element, and conductive element 33 may extend longitudinally through internal lumen 27 and through shaft 14. As shown in FIG. 1B, fluid delivered through port 22 may surround at least a portion of conductive element 33. In another aspect, the energy source may be a part of handle 12.

As mentioned, handle 12 may control the extension or retraction of electrode 26 relative to the distal end 16 of shaft 14. For example, main body 18 may include a slot 34 and a thumb ring 36. Movable body 20 may be slidably positioned within slot 34 and include one or more finger holes 38. Movable body 20 may be coupled to a drive element, and the drive element may impart distal or proximal movement to at least a portion of electrode 26 based on relative movement between main body 18 and movable body 20. In one aspect, conductive element 33 may also be a drive wire, rod, cable, or the like, such that conductive element 33 imparts distal or proximal movement to at least a portion of electrode 26 while also coupling electrode 26 to hub 24, e.g., the one or more prongs 32, to deliver the energy to electrode 26.

As shown in FIG. 1C, handle 12 may also include a locking mechanism to selectively secure movable body 20 at a predetermined position along slot 34, and/or within a predetermined range of positions along slot 34, to releasably fix the relative positions of main body 18 and movable body 20, and, thus, of electrode 26 and shaft 14. It is noted that port 22 is omitted in FIG. 1C for clarity. For example, handle 12 may include a locking component 39A coupled to movable body 20. Locking component 39A may be positioned within slot 34 between movable body 20 and main body 18. Locking component 39A includes a thumb depression 39B, a locking ramp 39C, and a lock retention clip 39D.

Locking component 39A may have an unlocked state and a locked state. In the unlocked state, locking component 39A may move in tandem with movable body 20 relative to main body 18. In the locked state, locking component 39A may lock the position of movable body 20 within slot 34 due to locking ramp 39C abutting a distal portion of movable body 20 and filling the gap (e.g., wedging) between movable body 20 and main body 18. The locking state may be achieved when a user applies a force on locking component 39A (e.g., via thumb depression 39B), and moving locking component 39A proximally relative to movable body 20 and/or moving movable body 20 distally relative to locking component 39A, to position movable body 20 on locking ramp 39C. The user may release locking component 39A from the locking state by moving locking component 39A distally relative to movable body 20 and/or moving movable body 20 proximally relative to locking component 39A. Additionally, locking component 39A may include a living spring or hinge (not shown) biasing thumb depression 39B outward from locking ramp 39C, away from slot 34. In this aspect, a user may depress thumb depression 39B to facilitate locking. Releasing thumb depression 39B may facilitate unlocking, allowing locking component 39A to slide relative to main body 18 to any other position for subsequent locking. Lock retention clip 39D may help to ensure that movable body 20 does not slide proximally off of locking component 39A.

Shaft 14 extends from a distal portion of main body 18 to distal end 16, and may surround at least a portion of electrode 26. Shaft 14 may be coupled to handle 12 via a coupler 40, which may surround a portion of shaft 14 and screw onto main body 18 to secure the elements. Shaft 14 may be a sheath that surrounds at least a portion of the central lumen and the drive wire. In another aspect, shaft 14 may be an extrusion that includes one or more lumens extending from handle 12 to distal end 16.

Figure 2C:
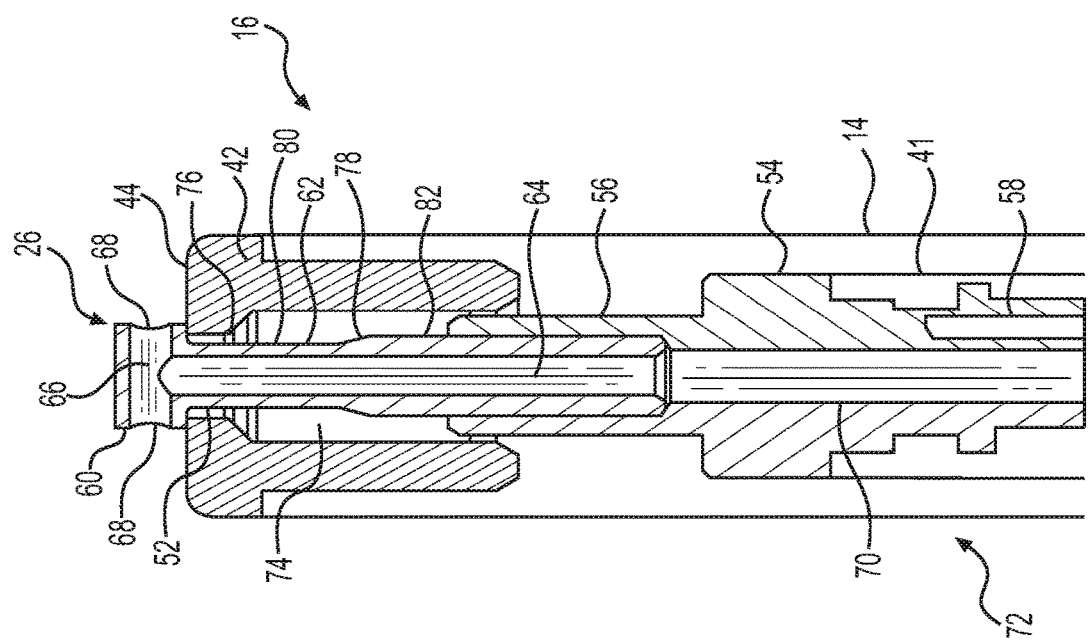
FIGS. 2A-2C illustrate various views of a distal portion of the medical device of FIG. 1, according to aspects of the present disclosure.
Figure 2B:
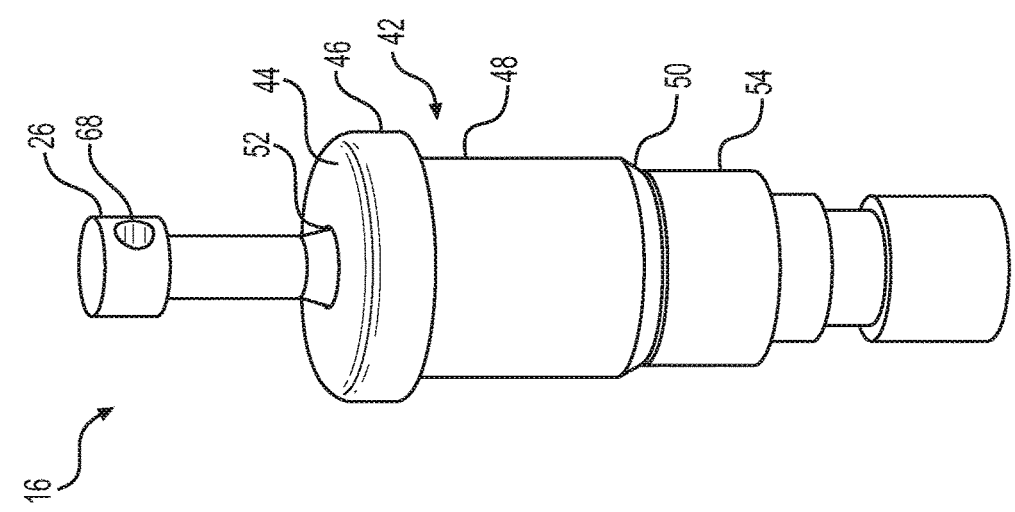
Figure 2A:
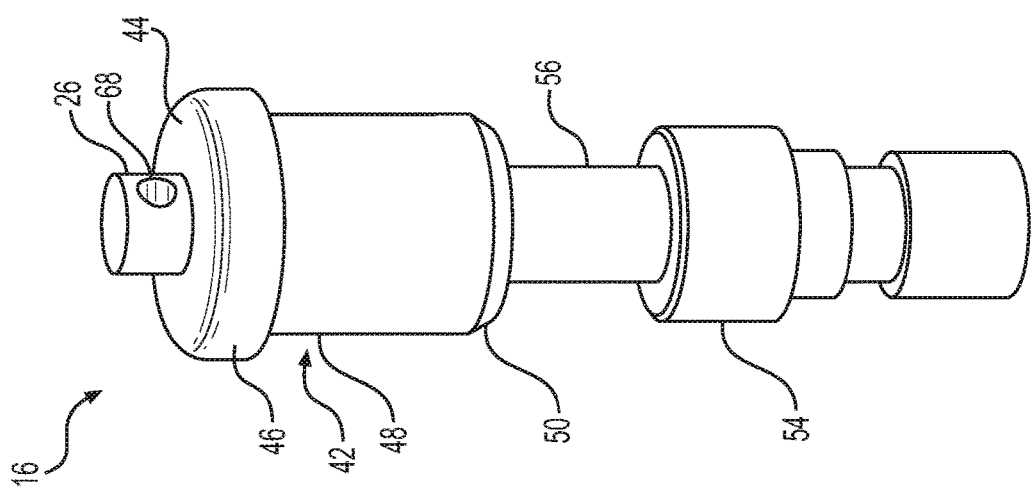

FIGS. 2A-2C illustrate additional aspects of distal end 16. It is noted that FIGS. 2A and 2B illustrate the internal components of distal end 16, without showing the distal portion of shaft 14 that may radially surround at least a portion of distal end 16. FIG. 2C depicts distal end 16 with shaft 14 (e.g., an outer sheath) and an inner sheath 41 coupled to portions of distal end 16.

FIGS. 2A and 2B show perspective views of a portion of distal end 16, with a portion of electrode 26 positioned within an end cap 42 of distal end 16. End cap 42 may include a distal end face 44 and graduated surfaces 46, 48, and 50. For example, a first graduated surface 46 may be at a distalmost portion of end cap 42. As shown in FIG. 2C, with shaft 14 coupled to distal end 16, first graduated surface 46 of end cap 42 may be exposed distally beyond shaft 14, while a second graduated surface 48 may be received in shaft 14. A third graduated surface 50 may, for example, be tapered to facilitate insertion of end cap 42 into shaft 14. In another example, shaft 14 may fully enclose the radially exterior portions of end cap 42. End cap 42 may be at least partially electrically insulating. For example, end cap 42 may be formed of a ceramic material or another non-conductive material. Alternatively, only distal end face 44 and an internal portion of end cap 42 that contacts and/or surrounds electrode 26 may be electrically insulating. Distal end face 44 includes a central opening 52 (FIGS. 2B and 2C) through which electrode 26 may extend and retract.

Electrode 26 may be coupled to a proximal support 54 of distal end 16, which includes a cylindrical extension 56. Proximal support 54 may be coupled to a portion of the drive wire via a drive wire receiving portion 58 (FIG. 2C). Cylindrical extension 56 may extend distally and may receive at least a portion of electrode 26. Electrode 26 and cylindrical extension 56 may be coupled via welding, an adhesive, crimping, friction fit, or other appropriate coupling. In one aspect, cylindrical extension 56 may allow for different electrodes 26 to be removably coupled to distal end 16. Electrode 26 and proximal support 54 may be movable relative to end cap 42 in response to the relative movement of movable body 20 and main body 18 of handle 12. For example, with movable body 20 in a proximal position relative to main body 18, electrode 26 may be substantially retracted within end cap 42 with only a distal portion of electrode 26 extending distally beyond end cap 42 (FIG. 2A). Then, as movable body 20 is translated distally relative to main body 18, electrode 26 and proximal support 54 translate distally relative to end cap 42 such that a greater portion of electrode 26 extends distally beyond end cap 42 through central opening 52 (FIG. 2B).

Alternatively, although not shown, with movable body 20 in the proximalmost position, electrode 26 may be fully retracted within central opening 52 of end cap 42. Furthermore, in one aspect, movable member 20 may have an equilibrium position relative to main body 18, and the equilibrium position may correspond to electrode 26 being partially extended from end cap 42. It is noted that while central opening 52 is shown in FIGS. 2B and 2C as being smaller than a portion of electrode 26, this disclosure is not so limited, and central opening 52 and electrode 26 may include various sizes and arrangements. For example, central opening 52 may be wider than electrode 26 such that electrode 26 may be fully retracted within central opening 52. Alternatively, central opening 52 may be narrower than electrode 26 such that electrode 26 may always remain partially extended from central opening 52.

FIG. 2C depicts a cross-sectional view of a portion of distal end 16 shown in FIGS. 2A and 2B. Electrode 26 includes a distal tip 60 and a longitudinal portion 62. Distal tip 60 may be wider than longitudinal portion 62, and distal tip 60 may be wider than central opening 52, as discussed above. Electrode 26 also includes an electrode lumen 64 extending through longitudinal portion 62. Electrode lumen 64 is in fluid communication with port 22 via at least one lumen 70 through proximal support 54. In one aspect, inner sheath 41 may form at least a portion of the fluid connection between lumen 70 and port 22. Additionally, electrode lumen 64 is in fluid communication with a lumen or channel 66 within distal tip 60 that allows fluid to flow from electrode lumen 64 to at least one outlet 68. As shown in FIG. 2C, electrode 26 may include two outlets 68, and channel 66 may be an internal lumen arranged perpendicularly to or otherwise at an angle relative to electrode lumen 64. Outlets 68 may be arranged in any position and in any direction on electrode 26.

Proximal support 54 includes a proximal coupling portion 72, which includes drive wire receiving portion 58. Drive wire receiving portion 58 may be an indentation that extends parallel to at least a portion of lumen 70. Drive wire receiving portion 58 may receive a portion of a drive wire (not shown), and the drive wire and/or inner sheath 41 may be coupled to movable body 20 such that the movement of movable body 20 imparts distal or proximal movement to proximal support 54 and, thus, to electrode 26. The drive wire may be coupled to drive wire receiving portion 58 within coupling portion 72 by welding, an adhesive, crimping, friction fit, or any other permanent or temporary coupling. Proximal support 54 may also be coupled to electrode 26 by welding, an adhesive, crimping, friction fit, or any other permanent or temporary coupling. In one aspect, both the drive wire and proximal support 54 are conductive to electrically connect the one or more prongs 32 of hub 24 to electrode 26. In another aspect, proximal support 54 may be at least partially insulating, and may include a wire or other conductive element electrically connecting the drive wire to electrode 26. Similarly, in one aspect, the drive wire may be at least partially insulating and may include a wire or other conductive element. Furthermore, at least a portion of the drive wire may be positioned within inner sheath 41. Alternatively, the drive wire may be positioned within a separate lumen in shaft 14 (e.g., a lumen separate from the lumen running through inner sheath 41).

End cap 42 includes a central portion 74 through which electrode 26 may move during the extension and retraction. End cap 42 also includes a narrowing portion or stop surface 76 at a distal end of central portion 74. Electrode 26 may include a widened portion 78 between a first longitudinal portion 80 and a second longitudinal portion 82 of longitudinal portion 62. Stop surface 76 and widened portion 78 may limit the distal extension of electrode 26 through end cap 42. In a fully extended position, first longitudinal portion 80 may protrude from end cap 42 and may form an exposed portion that may be used for cutting or otherwise treating tissue. Additionally, although not shown, end cap 42 may be fixedly coupled to shaft 14 via welding, an adhesive, crimping, friction fit, or other appropriate coupling.

FIGS. 3A and 3B illustrate perspective and cross-sectional views, respectively, of electrode 26. As shown in FIGS. 3A and 3B, an axis A of channel 66 may be transverse (e.g., perpendicular, or at any other suitable angle) to an axis B of electrode lumen 64. Additionally, in this aspect, outlets 68 are positioned proximal to a distal face 84 of distal tip 60. Outlets 68 may provide at least two points of egress for the fluid introduced through port 22, with the central axes of the points of egress being offset, at an angle to, or otherwise different than (e.g., not collinear with) the axis B of electrode lumen 64. With outlets 68 being offset from axis B of electrode lumen 64, distal face 84 may be a closed end. Longitudinal portion 62 may be used as a cutting shaft, and distal face 84 may include a flat or domed portion that may be used to perform hemostasis or other tissue treatment.

Distal tip 60 may be a cylindrical portion of electrode 26, and may be wider than first longitudinal portion 80 of longitudinal portion 62 of electrode 26. Electrode 26 may be energized through a connection to hub 24 in any manner discussed above such that distal tip 60 may be applied to tissue or material to treat the tissue or material. Alternatively, distal tip 60 may be non-conductive and may help to prevent damage to underlying tissue while a user apply other portions of electrode 26 to treat tissue. Although outlets 68 are depicted as circular, it is noted that this disclosure is not so limited. Outlets 68 may be triangular, rectangular, pentagonal, oval, or any other appropriate shape.

Including two or more outlets 68 in electrode 26 may help to decrease the likelihood of the delivered fluid piercing, cutting, or otherwise damaging the tissue being treated. In one example, the channel 66 and/or outlets 68 may include a cross-sectional area greater than a cross-sectional area of electrode lumen 64, such that the pressure of the fluid may decrease as the fluid passes from electrode lumen 64 into channel 66 and/or outlets 68. Additionally, outlets 68 may help to deliver fluid in a way that surrounds electrode 26 (e.g., around distal tip 60), rather than delivering the fluid distal to distal tip 60. Fluid may be delivered to the tissue or material via outlets 68, with the fluid being delivered proximal to distal face 84 of distal tip 60 of electrode 26. This may provide the user with the ability to deliver fluid in a consistent way. For example, the fluid may be delivered so as to form one, unitary fluid or fluid/tissue pocket, or to form a series of closely spaced fluid or fluid/tissue pockets, within or under the tissue being treated, rather than a plurality of independent fluid pockets.

The position of outlets 68 proximal to distal face 84 may allow for the delivery of fluid when distal face 84 is abutting tissue, which would be difficult to do if fluid was emitted through a single outlet in line with axis B, since such an outlet would be partially or fully blocked by tissue abutting distal face 84. Also, the delivered fluid may be at a lower pressure than if delivered through a single distal outlet, since the fluid pressure will be divided amongst a plurality of outlets. Furthermore, the directional orientation of outlets 68 may help to deliver fluid within a submucosal plane beneath or between layers of tissue. Such fluid delivery may help to reduce the likelihood of piercing, harming, or affecting other tissue or tissue layers. The fluid delivery discussed herein may also help a user control the depth of the delivered fluid and/or control the size and inflation of one or more blebs in the tissue.

Other examples of electrodes are described in the paragraphs below. It should be understood that any feature described in connection with electrode 26 may be found in any of the other electrodes, and vice-versa. Aspects of the other electrodes also may be shared between them.

Figure 4B:
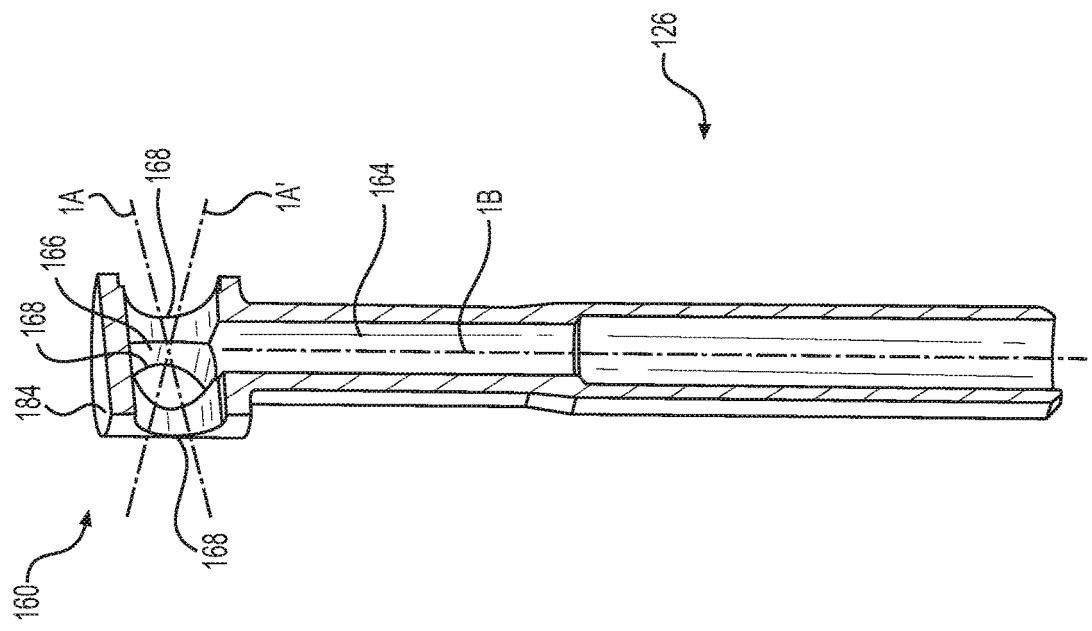
FIGS. 4A and 4B illustrate a perspective view and a cross-sectional view, respectively, of another portion of a medical device, according to aspects of the present disclosure.
Figure 4A:
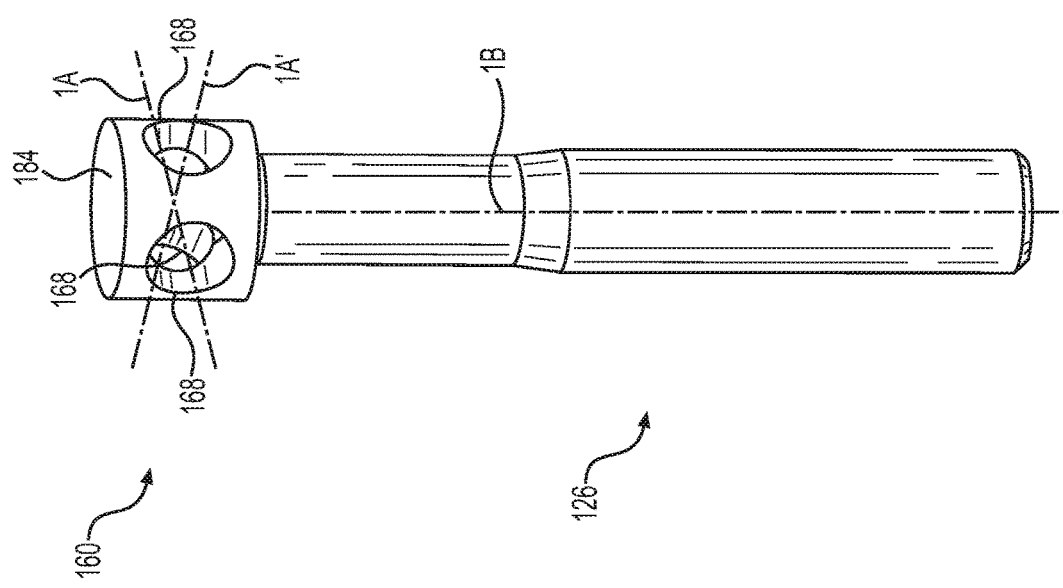

FIGS. 4A and 4B depict perspective and cross-sectional views, respectively, of another electrode 126 that may be positioned and function within medical device 10 as discussed with respect to electrode 26 above. Electrode 126 includes four outlets 168. While outlets 168 are shown as equally distributed on distal tip 160, this disclosure is not so limited, and outlets 168 may take various configurations on distal tip 160. For example, outlets 168 may be positioned unevenly around distal tip 160, and/or outlets 168 may be staggered and positioned at different longitudinal locations relative to axis 1B of electrode 126. As shown in FIGS. 4A and 4B, a channel 166 or two channels may include two axes 1A and 1A' connecting outlets 168, and both axes 1A and 1A' may be transverse (e.g., perpendicular or at any other suitable angle) to an axis 1B of electrode lumen 164. Axes 1A and 1A' may be transverse (e.g., perpendicular or at any other suitable angle) to each other, or may take other arrangements based on the desired location and positions of outlets 168. As discussed above, outlets 168 are positioned proximal to distal face 184 of distal tip 160, so fluid may be delivered to tissue or material via outlets 168 with the fluid being emitted from locations proximal to distal face 184, and at an angle relative to internal electrode lumen 164.

Figure 5B:
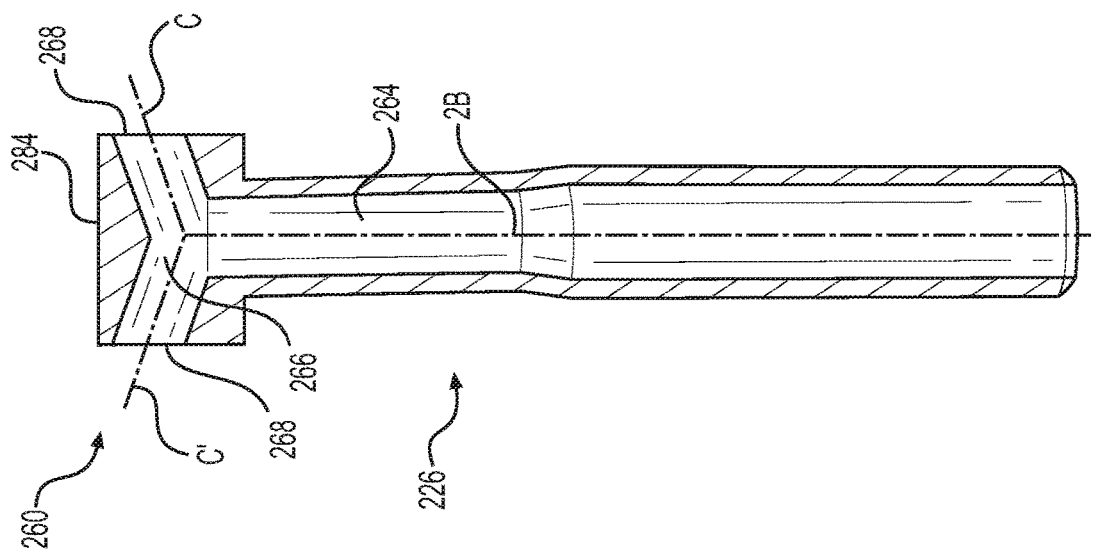
FIGS. 5A and 5B illustrate a perspective view and a cross-sectional view, respectively, of another portion of a medical device, according to aspects of the present disclosure.
Figure 5A:
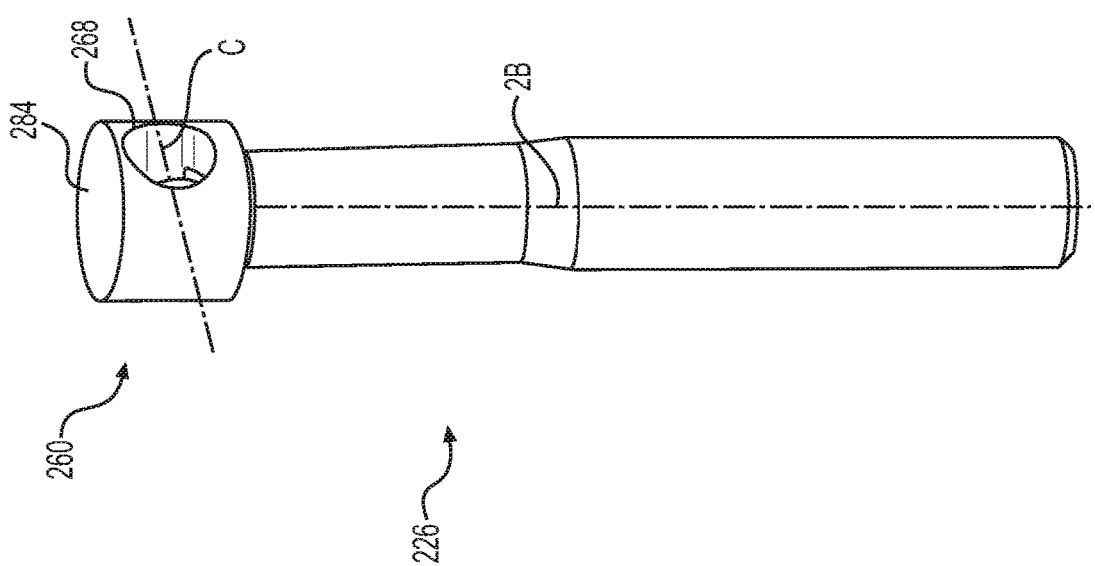

FIGS. 5A and 5B depict perspective and cross-sectional views, respectively, of an additional aspect of an electrode 226 that may be positioned and function within medical device 10 as discussed with respect to electrode 26 above. Electrode 226 includes two outlets 268, which may be positioned on opposite sides of distal tip 260. As shown in FIG. 5B, electrode 226 includes two channels, which may form a V-shaped channel 266, to connect lumen 264 to outlets 268. Channels 266 may be positioned at an angle within distal tip 260 such that fluid may delivered at an angle relative to the longitudinal axis 2B of lumen 264 and/or to distal face 284. In one aspect, channels 266 may include axes C and C' and connect to electrode lumen 264 at acute angles. For example, channels 266 may connect to electrode lumen 264 at an angle of approximately 60 degrees, approximately 45 degrees, approximately 30 degrees, or approximately 15 degrees. In another aspect, each of channels 266 may connect to electrode lumen 264 at a different angle. In another aspect, channel 266 and outlets 268 may be arranged such that axes C and C' are not co-planar.

FIGS. 6A-6D depict perspective views of additional aspects of the present disclosure. Particularly, FIGS. 6A-6D illustrate portions of various electrodes 326, 426, 526, and 626 that may be positioned and function within medical device 10 as discussed with respect to electrode 26 above.

Figure 6A:
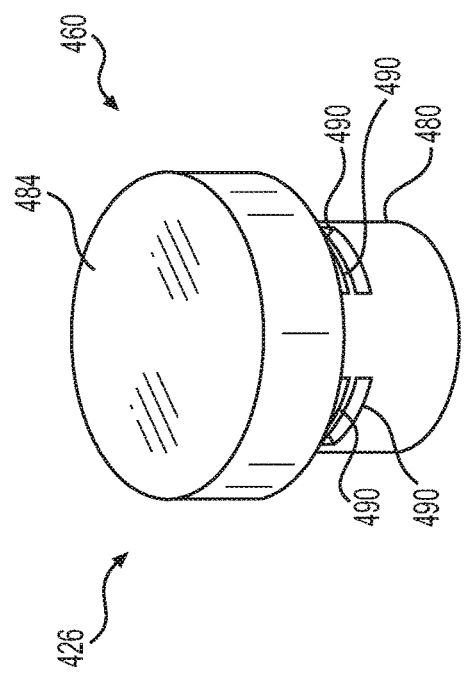
FIGS. 6A-6D illustrate perspective views of other portions of a medical device, according to further aspects of the present disclosure.

FIG. 6A illustrates electrode 326 with distal tip 360 and a portion of first longitudinal portion 380. In this aspect, distal tip 360 includes a plurality, for example, two, three, or four (as shown) indentations 386 in distal face 384. Indentations 386 may intersect in a middle portion (not shown) of distal tip 360 with the electrode lumen (not shown), as discussed with outlets 68. Indentations 386 may be semicircular cutout portions of distal tip 360, or may have any other suitable shape, and may be perpendicular, transverse, or otherwise at an angle to the electrode lumen and the central longitudinal axis of electrode 326. Electrode 326 also includes an electrode cap 388. Electrode cap 388 may be a circular disc (either domed or flat), and may be coupled to distal tip 360 via the non-indented portions of distal face 384, for example, via welding, an adhesive, or another appropriate connection. Electrode cap 388 is positioned on distal tip 360 to cover the intersection of indentations 386 and the electrode lumen. As such, distal tip 360, including electrode cap 388 may be positioned adjacent to or within tissue to apply energy to the tissue. Additionally, fluid may be delivered via the electrode lumen, with indentations 386 and electrode cap 388 diverting the flow of the fluid at least partially transverse to the longitudinal axis of electrode 326. In this example, the emission of the fluid may be at locations proximal to the distalmost portion of electrode 326 formed by electrode cap 388.

Figure 6B:
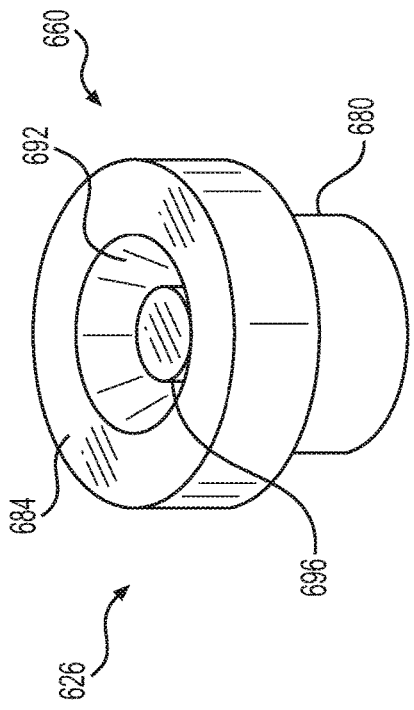

FIG. 6B illustrates electrode 426 with distal tip 460 and a portion of first longitudinal portion 480. In this aspect, distal tip 460 may be an at least partially cylindrical disc. Additionally, first longitudinal portion 480 may include side slits 490 that extend through first longitudinal portion 480 into the electrode lumen. In one aspect, electrode 426 may include pairs or sets of side slits 490 positioned around first longitudinal portion 480 proximal to distal tip 460. For example, four pairs of side slits 490 may be evenly or unevenly distributed around first longitudinal portion 480. Side slits 490 may be rectangular (as shown), oval, circular, or another appropriate shape. As such, distal tip 460 may be positioned adjacent to or within tissue to apply energy to the tissue. Additionally, fluid may be delivered via the electrode lumen, with side slits 490 diverting the flow of the fluid at least partially transverse to the longitudinal axis of electrode 426 and proximal to distal face 484 of electrode 426.

Figure 6C:
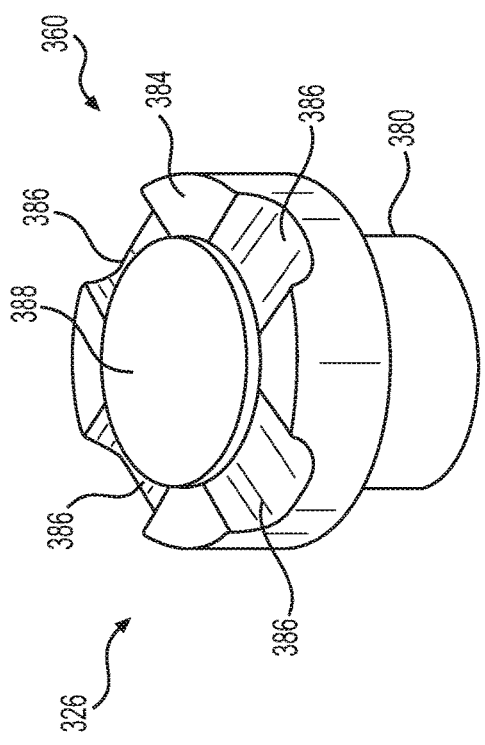

FIG. 6C illustrates electrode 526 with distal tip 560 and a portion of first longitudinal portion 580. As shown, distal tip 560 may be an at least partially cylindrical disc, and may include a distal opening 592 connecting to the electrode lumen within electrode 526. In one aspect, distal opening 592 forms a truncated cone connecting distal face 584 to the electrode lumen (not shown). Distal opening 592 also includes a divider 594 positioned within distal opening 592 and at least partially bisecting distal opening 592. In one instance, divider 594 may be narrower at a proximal portion and wider at a distal portion. As such, distal tip 560 may be positioned adjacent to or within tissue to apply energy to the tissue. Additionally, fluid may be delivered via the electrode lumen, with distal opening 592 and divider 594 diverting the flow of the fluid to flow at an angle relative to or at least partially transverse to the longitudinal axis of electrode 526. Furthermore, although not shown, distal tip 560 may include a plurality of dividers 594. For example, distal tip 560 may include two or more parallel dividers 594, or may include a plurality of dividers 594 that intersect in distal opening 592 to divert the flow of fluid to flow at an angle relative to or at least partially transverse to the longitudinal axis of electrode 526.

Figure 6D:
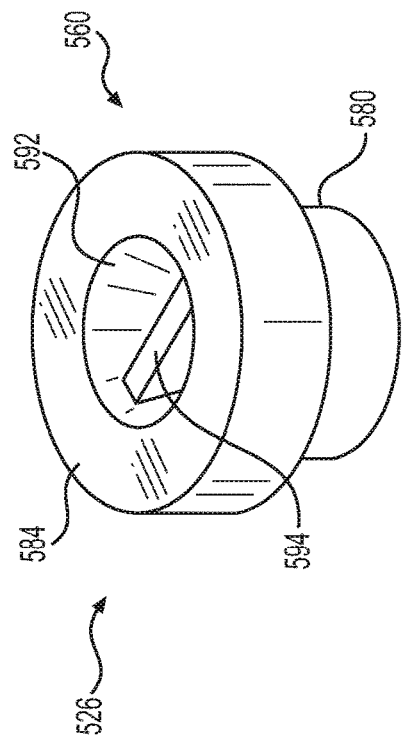

FIG. 6D illustrates electrode 626 with distal tip 660 and a portion of first longitudinal portion 680. As shown, distal tip 660 may be an at least partially cylindrical disc, and may include a distal opening 692 connecting to the lumen within electrode 626. In this aspect, distal opening 692 forms a truncated cone connecting distal face 684 to the electrode lumen (not shown). Distal opening 692 also includes a spreader 696 positioned within distal opening 692. Spreader 696 may be ball-shaped, cylindrical, an inverted cone, or another appropriate shape, and may be coupled to an interior portion of distal opening 692 or electrode lumen by one or more standoffs. As such, distal tip 660 may be positioned adjacent to or within tissue to apply energy to the tissue. Additionally, fluid may be delivered via the electrode lumen, with distal opening 692 and spreader 696 diverting the flow of the fluid to flow at an angle to or at least partially transverse to the longitudinal axis of electrode 626.

Figure 7:
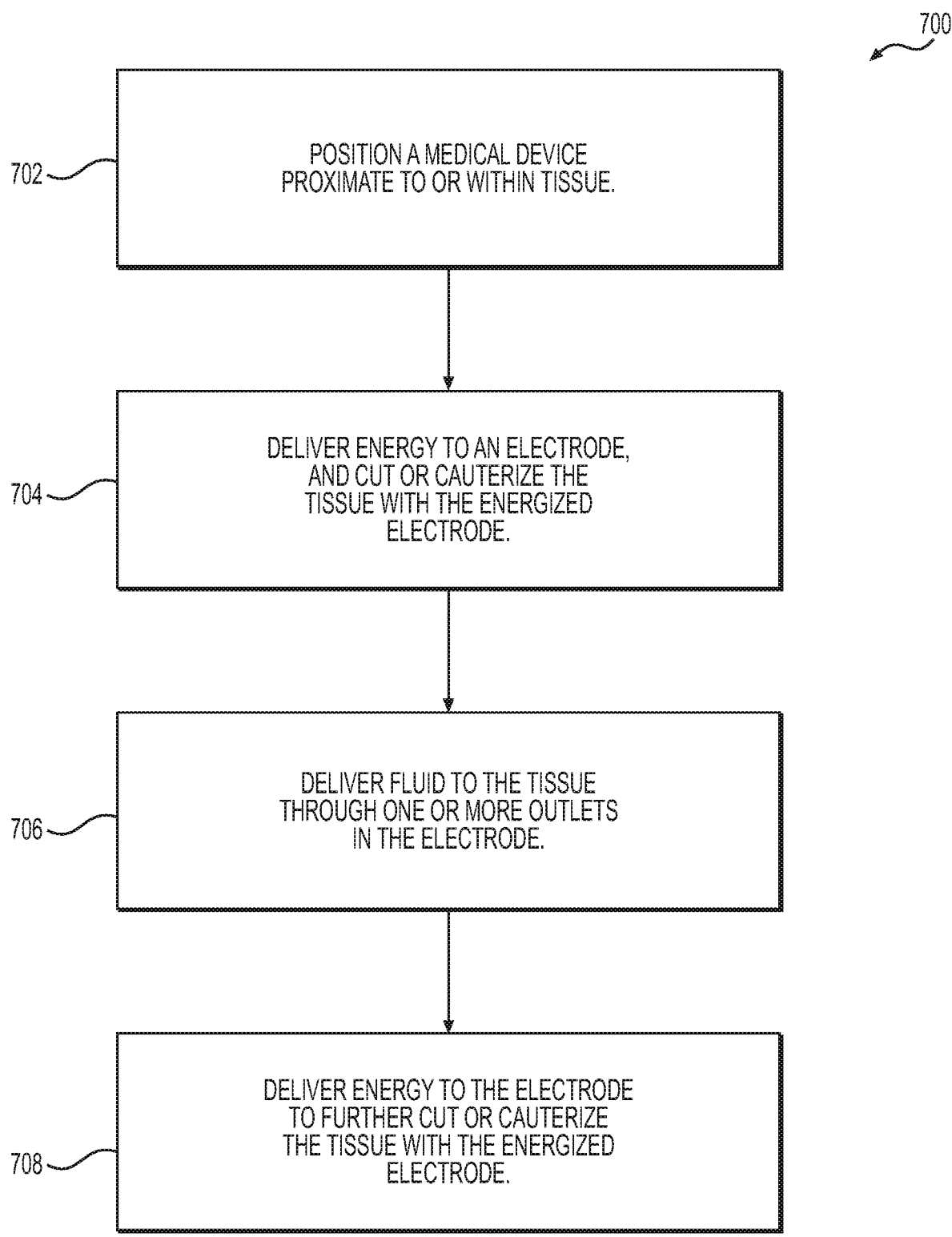
FIG. 7 is a flow diagram of an exemplary tissue treatment method, according to aspects of the present disclosure.

FIG. 7 is a flow diagram portraying an exemplary tissue treatment method 700 to apply energy and deliver fluid for at least one tissue resection or cautery procedure. Method 700 includes a step 702, wherein the user positions the medical device proximate or within tissue. Step 702 may include a preliminary step of injecting a fluid into the tissue with a separate conventional needle injector. The preliminary injection may separate or expand one or more layers of tissue, beneath or containing a diseased portion of tissue, to lift the diseased tissue away from underlying layers of tissue, thereby creating a tissue bleb. Step 702 may also include delivering the medical device through an insertion device. In a step 704, the user may deliver energy to an electrode, and may apply the energized electrode to the tissue in order to cut, dissect, ablate, mark, coagulate, cauterize, or otherwise treat the tissue. Step 704 may include extending or retracting electrode 26 by action on movable body 20 of handle 12 relative to main body 18, as discussed above. Additionally, the energy may be delivered to electrode 26 from an energy source, which may be controlled by a user interface.

Method 700 further includes a step 706, which includes delivering fluid to the tissue through one or more outlets in the electrode. Step 706 may help to form, re-form, maintain, and/or enlarge a bleb in the tissue. The outlets in the electrode may be any configuration of outlets 68, 168, and 268; indentations 386; side slits 490; or distal openings 592 and 692 discussed above. As such, the fluid is delivered at an angle relative to a longitudinal axis of the electrode. Additionally or alternatively, the fluid is delivered proximal to the distal end face of the electrode. The fluid may be delivered to electrode 26 from a fluid source, which may be controlled by the user interface.

Then, method 700 may include a step 708, in which the user may again deliver energy to the electrode to further cut, dissect, ablate, mark, coagulate, cauterize, or otherwise treat the tissue with the energized electrode. Based on the type of medical procedure and progress of the tissue treatment, the user may repeat the steps of method 700 as many times as necessary to perform the tissue treatment procedure. For example, the user may cycle back from step 708 to step 702. Alternatively, the user may cycle back-and-forth between steps 706 and 708. Additionally, the delivery of the energy and fluid discussed in steps 704, 706, and 708 may be performed contemporaneous or may be staggered depending on the medical procedure.

The medical devices and methods discussed above allow a user to treat tissue by delivering electrical energy into the tissue, and injecting fluid into and/or under the tissue, either simultaneously or sequentially. Because outlets 68, 168, and 268; indentations 386; side slits 490; or distal openings 592 and 692 are positioned to deliver fluid at an angle relative to a central longitudinal axis of electrode 26, and/or are proximal to distal faces of their respective electrodes, the user may bring electrode 26 into abutment with tissue, while still having the ability to deliver fluid into and/or under the abutted tissue through the outlets. Moreover, because the medical device includes outlets 68, 168, and 268; indentations 386; side slits 490; or distal openings 592 and 692, fluid may still be delivered to the tissue if one fluid exit, or part of a fluid exit, is obstructed by tissue or otherwise becomes blocked. In addition, the existence of multiple egresses allows fluid to be emitted without requiring an increased amount of pressure from the fluid supply. As such, the medical devices and methods discussed herein may help a user to form, maintain, or enlarge a bleb in tissue during a procedure to cut, dissect, ablate, mark, coagulate, cauterize, or otherwise treat tissue. It is further noted that the different configurations of distal ends 14 and electrodes 26, 126, 226, 326, 426, 526, and 626 discussed herein may be interchangeable in order to customize a medical device for a particular procedure. Specifically, a medical device may include a generic distal end 16, and one of the different electrodes 26, 126, 226, 326, 426, 526, and 626 may be selectively coupled to distal end 16 in order to apply energy and deliver fluid to tissue, with each electrode providing a specific configuration for the user.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device comprising:
   a shaft including a central lumen configured to direct a flow of fluid through the shaft;
   a proximal support movable within a distal portion of the shaft, wherein a distal portion of the proximal support includes a cylindrical extension, wherein the proximal support includes a lumen, wherein a proximal portion of the proximal support includes a drive element receiving portion to receive a portion of a drive element, wherein movement of the drive element controls the movement of the proximal support within the distal portion of the shaft; and
   an electrode positioned at a distal portion of the shaft and including an electrode lumen in fluid communication with the central lumen via the lumen of the proximal support, wherein a portion of the electrode is received within the cylindrical extension, wherein the electrode lumen is configured to receive the flow of fluid from the central lumen via the lumen of the proximal support, wherein the electrode includes a longitudinal portion and a distal tip at a distal end of the longitudinal portion, wherein the distal tip is cylindrical with a flat distal end, is wider than the longitudinal portion, and is wider than the central lumen,
   wherein the distal tip of the electrode includes one or more channels angled relative to the electrode lumen, wherein the one or more channels are in fluid communication with the electrode lumen to receive the flow of fluid from the electrode lumen, and wherein the one or more channels are configured to divert the flow of fluid from the electrode lumen toward one or more outlets laterally offset from the electrode lumen, and
   wherein the shaft or a combination of the electrode and the proximal support is movable relative to the other of the shaft or the combination of the electrode and the proximal support.

2. The medical device of claim 1, further including a handle with a main part and a movable part, and wherein at least one of the main part and the movable part includes a slot, sliding of the movable part in a first direction relative to the main part extends the electrode, and sliding of the movable part in a second direction relative to the main part retracts the electrode.

3. The medical device of claim 2, wherein at least one of the main part and the movable part includes a fluid port to couple a fluid source to the handle, and wherein at least one of the main part and the movable part includes a hub to couple an energy source to the handle.

4. The medical device of claim 3, further including the drive element, wherein the drive element extends from the handle to the electrode via the proximal support to electrically connect the energy source to the electrode, and to move the electrode distally or proximally based on relative movement between the main part and the movable part.

5. The medical device of claim 4, further including a one way valve coupling the fluid source to the port and preventing fluid from flowing proximally out of the port.

6. The medical device of claim 1, wherein the shaft includes an electrically insulating sheath, and wherein the sheath is coupled to an electrically insulating distal end cap including a passage for slidably receiving the electrode.

7. The medical device of claim 1, wherein the distal tip includes a closed distalmost end face, wherein the distal tip includes at least two outlets for emitting the fluid, and wherein the at least two outlets are positioned proximal to the distalmost end face.

8. The medical device of claim 7, wherein one or more central longitudinal axes of the one or more channels extend transverse to a central longitudinal axis of the electrode lumen.

9. The medical device of claim 7, wherein the one or more channels extend in a V-shape to connect the electrode lumen to the two outlets.

10. The medical device of claim 7, wherein the distal tip includes four outlets, and wherein the four outlets are connected by two channels, the two channels extending in a direction transverse to the electrode lumen.

11. The medical device of claim 1, wherein the one or more channels includes a plurality of indentations that connect a radial exterior of the distal tip to the electrode lumen, and wherein the electrode further includes an electrode cap that extends over a distal end of the electrode lumen such that fluid delivered through the electrode lumen flows through the indentations at an angle relative to a central longitudinal axis of the electrode lumen.

12. The medical device of claim 1, wherein the distal tip extends over a distal end of the electrode lumen, and wherein the one or more channels and one or more outlets are formed by a plurality of side slits positioned proximal to the distal end of the distal tip and connecting to the electrode lumen such that fluid delivered through the electrode lumen flows through the side slits at an angle relative to a central longitudinal axis of the electrode lumen.

13. The medical device of claim 1, further including an insulating end cap surrounding at least a portion of the electrode, wherein the end cap includes a narrowed stop surface radially surrounding a portion of the electrode, wherein the electrode includes a widened portion proximal to the distal tip of the electrode, and wherein the stop surface of the end cap and the widened portion of the electrode limit the distal extension of the electrode.

14. A medical device comprising:
   a shaft including a central lumen configured to direct a flow of fluid through the shaft;
   a proximal support movable within a distal portion of the shaft, wherein the proximal support includes a lumen in communication with the central lumen, wherein a proximal portion of the proximal support includes a drive element receiving portion to receive a portion of a drive element, wherein movement of the drive element controls the movement of the proximal support within the distal portion of the shaft; and
   an electrode positioned at a distal portion of the shaft and including an electrode lumen in fluid communication with the central lumen via the lumen of the proximal support, wherein the electrode lumen is configured to receive the flow of fluid from the central lumen via the lumen of the proximal support, and wherein the electrode lumen includes a central longitudinal axis;
   wherein the electrode includes a longitudinal portion and a distal tip at a distal end of the longitudinal portion, and wherein the longitudinal portion includes a first longitudinal portion, a second longitudinal portion, and a widened portion between the first longitudinal portion and the second longitudinal portion, wherein the distal tip includes a plurality of channels fluidly connected to the electrode lumen, wherein the distal tip includes a radial thickness that is wider than a radial thickness of the longitudinal portion, wherein the radial thickness of the distal tip is also wider than the central lumen, wherein each of the plurality of channels includes a central longitudinal axis, and wherein at least one of the central longitudinal axes of the plurality of channels is angled relative to the central longitudinal axis of the electrode lumen, wherein a distal portion of the proximal support includes an extension, wherein the extension is coupled to and at least partially overlaps with a portion of the electrode, such that movement of the proximal support extends or retracts the proximal support and the electrode.

15. The medical device of claim 14, wherein a combined cross-sectional area of the plurality of channels is greater than a cross-sectional area of the electrode lumen.

16. The medical device of claim 14, wherein the plurality of channels includes two channels, with the central longitudinal axes of the two channels extending in a V-shape and being angled relative to the central longitudinal axis of the electrode lumen by an acute angle.

17. The medical device of claim 14, wherein the distal tip includes a closed distalmost end face, and wherein the shaft or the electrode is movable relative to the other of the shaft or the electrode.

18. A method of treating tissue, comprising:
  inserting a medical device into a body lumen, wherein the medical device includes a shaft with a central lumen, a proximal support movable within a distal portion of the shaft, a drive element, and an electrode at a distal end of the medical device,
    wherein a distal portion of the proximal support includes an extension that receives a portion of the electrode, wherein the proximal support includes a lumen, wherein a proximal portion of the proximal support includes a drive element receiving portion to receive a portion of the drive element, wherein the proximal support includes a lumen, wherein movement of the drive element controls the movement of the proximal support within the distal portion of the shaft,
    wherein the electrode includes a longitudinal portion and a distal tip at a distal end of the longitudinal portion, wherein the distal tip includes a radial thickness that is wider than a radial thickness of the longitudinal portion, wherein the radial thickness of the distal tip is also wider than a radial thickness of the central lumen, wherein the distal tip of the electrode includes at least two fluid outlets positioned proximal to a distal face of the electrode, and wherein at least one fluid outlet includes a central axis that is transverse to a central longitudinal axis of the electrode;
  delivering fluid to a tissue portion within the body lumen, wherein the fluid is delivered through the central lumen of the shaft, the lumen of the proximal support, a lumen of the electrode, and through the at least two outlets into the tissue portion and is configured to at least partially move the tissue portion away from an underlying tissue layer; and
  energizing the electrode by delivering energy through the drive element and the proximal support to the electrode, and applying the energized electrode to the tissue portion to deliver electrical energy to the tissue portion.

19. The method of claim 18, further including:
  extending or retracting the electrode relative to the shaft via movement of the drive element and the proximal support, wherein the shaft further includes an insulating end cap surrounding at least a portion of the electrode, wherein the end cap includes a narrowed stop surface radially surrounding a portion of the electrode, wherein the electrode includes a widened portion proximal to a distal tip of the electrode, wherein the stop surface of the end cap and the widened portion of the electrode limit the distal extension of the electrode, and wherein the radial thickness of the distal tip of the electrode and the radial thickness of the central lumen limit the proximal retraction of the electrode;
  delivering fluid to the tissue portion another time after applying the energized electrode to the tissue portion; and
  resecting the tissue portion.

20. The method of claim 18, wherein inserting the medical device into the body lumen includes piercing the tissue portion with the electrode;
  wherein delivering fluid to the tissue portion within the body lumen includes delivering the fluid peripherally about the electrode; and
  wherein the method further includes contemporaneously delivering fluid and applying electrical energy to the electrode to resect the tissue portion with the energized electrode.

* * * * *